United States Patent [19]

MacLean et al.

[11] Patent Number: 5,726,207

[45] Date of Patent: Mar. 10, 1998

[54] PROTECTION OF ISCHEMIC MYOCARDIUM AGAINST REPERFUSION DAMAGE

[75] Inventors: David B. MacLean; David D. Thompson, both of Groton, Conn.

[73] Assignee: Pfizer Inc., New York, N.Y.

[21] Appl. No.: 805,040

[22] Filed: Feb. 21, 1997

Related U.S. Application Data

[60] Provisional application No. 60/012,401 Feb. 28, 1996.

[51] Int. Cl.$^6$ ............................................. A61K 31/135
[52] U.S. Cl. ................................................. 514/648
[58] Field of Search ..................................... 514/646

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Kazuaki et al. | 514/648 |
| 5,384,332 | 1/1995 | Fontana | 514/651 |
| 5,426,123 | 6/1995 | Fontana | 514/651 |
| 5,441,986 | 8/1995 | Thompson | 514/648 |
| 5,455,275 | 10/1995 | Fontana | 514/648 |
| 5,550,164 | 8/1996 | Fontana | 514/648 |

FOREIGN PATENT DOCUMENTS

WO96/02243  2/1996  WIPO.

OTHER PUBLICATIONS

Wiseman, Trends Pharmacol. Sci, 15, No. 3, pp. 83–89 (1994).

Wiseman, H. et al., "Droloxifene (3-hydroxytamoxifen) has membrane antioxidant ability: potential relevance to its mechanism of therapeutic action in breast cancer," *Cancer Letters*, 66 (1992) 61–68.

Hale, S. L., et al., "Estradiol, Administered Acutely, Protects Ischemic Myocardium in Both Female and Male Rabbits," *J. Am. Coll. Cardiol.*, 25 189A, 1995.

Primary Examiner—Jerome D. Goldberg
Attorney, Agent, or Firm—Peter Richardson; Gregg C. Benson; Mervin E. Brokke

[57] ABSTRACT

The present invention provides novel methods of inhibiting reperfusion damage in ischemic myocardium comprising administering to a mammal in need of such treatment an effective amount of a compound of formula I

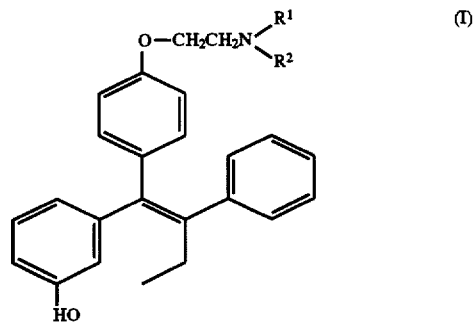

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

3 Claims, No Drawings

PROTECTION OF ISCHEMIC MYOCARDIUM AGAINST REPERFUSION DAMAGE

This is a continuation of provisional application Ser. No. 60/012,401 filed Feb. 28, 1996, the benefit of which is hereby claimed under 37 C.F.R. §1.78(a)(3).

BACKGROUND OF THE INVENTION

Premenopausal women are at lower risk of coronary heart disease than their male counterparts, and it has been shown that estrogen treatment protects against cardiovascular disease in postmenopausal women. Hale and Kloner have shown that acute pretreatment with estradiol reduced myocardial infarct size caused by occlusion of the coronary artery in both male and female rabbits, thus demonstrating that estrogen exerts a protective effect on ischemic myocardium that is not associated with an increase in myocardial blood flow or alteration in neurodynaines. J. Am. Coll. Cardiol. 25, 189A (1995).

SUMMARY OF THE INVENTION

The present invention relates to methods for inhibiting reperfusion damage in ischemic myocardium comprising administering to a mammal in need of such treatment an effective amount of a compound of formula I

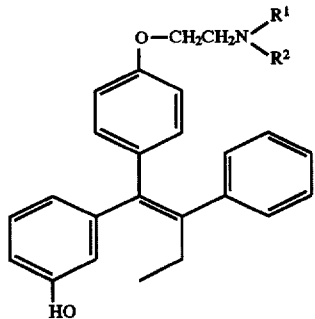

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen or a benzyl group; or a pharmaceutically acceptable salt thereof. A preferred compound of formula I is that in which $R^1$ and $R^2$ are methyl. A preferred salt is the citrate salt.

DETAILED DESCRIPTION OF THE INVENTION

The present invention concerns methods for inhibiting reperfusion damage in ischemic myocardium. The term "inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

Reperfusion leads to development of myocardial cell swelling, accumulation of calcium in mitochondria, accelerated washout of cellular enzymes, and the presence of characteristic contraction bands. These contraction bands are the morphologic markers of reperfusion injury, indicating that myocardial cells have been ischemically damaged and then subsequently supplied with oxygenated blood. For example, they are seen in acute subendocardial infarction throughout the necrotic zone, and they have been described following coronary bypass grafting of patients with acute myocardial ischemia, where they are thus secondary to surgical reperfusion. They may also be observed along the periphery of transmural infarctions, often associated with focal mitochondrial calcification. Compounds of the present invention are especially useful in preventing reperfusion damage of ischemic myocardium associated with coronary bypass surgery or with the use of the thrombolytic agents, streptokinase and tissue plasminogen activator. The compounds of the invention may be administered prophylactically, for example, prior to bypass surgery or concurrently with thrombolytic agents.

The methods of this invention are practiced by administering to an individual in need of treatment an effective amount of a compound formula I

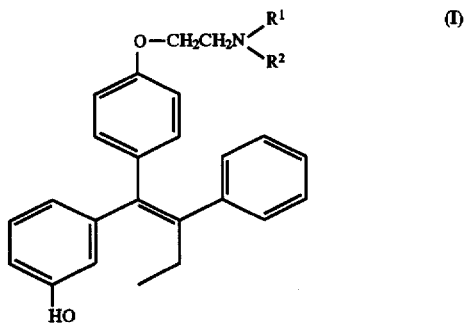

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 100 mg/day of a compound of the present invention. Preferred daily doses generally will be from about 1 mg to about 40 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–400 mg of active ingredient are made up as follows:

Formulation 3: Tablets

| Ingredient | Quantity (mg/tablet) |
|---|---|
| Active ingredient | 0.25–400 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

ASSAY

Ten male and ten female rabbits are treated with 1 mg of a compound of formula I. After 15 minutes, the rabbits are anesthetized and the coronary arteries are occluded for 30 minutes followed by four hours of reperfusion.

Comparable control groups are treated with vehicle.

The risk zone is assessed by blue dye and the infarct zone by tetrazolium staining. A reduced size of infarct zone relative to the control shows that the compound of formula I is effective in inhibiting reperfusion damage to ischemic myocardium.

We claim:

1. A method for inhibiting reperfusion damage in ischemic myocardium comprising administering to a mammal in need of such treatment an effective amount of a compound of formula I

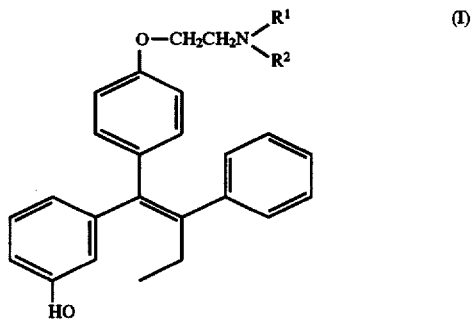

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

* * * * *